United States Patent
Averbuch et al.

(10) Patent No.: US 10,478,092 B2
(45) Date of Patent: *Nov. 19, 2019

(54) HYBRID REGISTRATION METHOD

(71) Applicant: Covidien LP, Mansfield, MA (US)

(72) Inventors: Dorian Averbuch, Ramat Hasharon (IL); Oded Zur, Kochav-Ya'ir Zur Yigal (IL); Oren P. Weingarten, Herzliya (IL)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/372,776

(22) Filed: Apr. 2, 2019

(65) Prior Publication Data

US 2019/0223760 A1 Jul. 25, 2019

Related U.S. Application Data

(63) Continuation of application No. 15/055,698, filed on Feb. 29, 2016, now Pat. No. 10,285,623, which is a continuation of application No. 13/875,685, filed on May 2, 2013, now Pat. No. 9,271,803, which is a continuation of application No. 13/287,883, filed on Nov. 2, 2011, now Pat. No. 8,452,068, which is a continuation of application No. 12/478,573, filed on Jun. 4, 2009, now Pat. No. 8,218,847.

(60) Provisional application No. 61/059,669, filed on Jun. 6, 2008.

(51) Int. Cl.
| | |
|---|---|
| A61B 5/06 | (2006.01) |
| A61B 34/20 | (2016.01) |
| G06T 7/33 | (2017.01) |
| A61B 1/267 | (2006.01) |
| A61B 5/00 | (2006.01) |
| G06T 7/00 | (2017.01) |
| A61B 90/00 | (2016.01) |
| A61B 17/00 | (2006.01) |

(52) U.S. Cl.
CPC ............ *A61B 5/066* (2013.01); *A61B 1/2676* (2013.01); *A61B 5/06* (2013.01); *A61B 5/064* (2013.01); *A61B 5/7246* (2013.01); *A61B 34/20* (2016.02); *G06T 7/0016* (2013.01); *G06T 7/33* (2017.01); *A61B 90/361* (2016.02); *A61B 2017/00699* (2013.01); *A61B 2034/2072* (2016.02); *A61B 2090/365* (2016.02); *A61B 2090/3762* (2016.02); *A61B 2576/00* (2013.01); *G06T 2207/10068* (2013.01); *G06T 2207/10081* (2013.01); *G06T 2207/30061* (2013.01)

(58) Field of Classification Search
CPC ....... A61B 5/06; A61B 5/064; A61B 19/5244; A61B 34/20; A61B 1/2676; A61B 5/7246; A61B 5/066; G06T 7/33

USPC .......................................................... 382/131
See application file for complete search history.

(56) References Cited

U.S. PATENT DOCUMENTS

| | | | |
|---|---|---|---|
| 1,576,781 | A | 3/1926 | Philips |
| 1,735,726 | A | 11/1929 | Bornhardt |
| 2,407,845 | A | 9/1946 | Nemeyer |
| 2,650,588 | A | 9/1953 | Drew |
| 2,697,433 | A | 12/1954 | Zehnder |
| 3,016,899 | A | 1/1962 | Stenvall |
| 3,017,887 | A | 1/1962 | Heyer |
| 3,061,936 | A | 11/1962 | De |
| 3,073,310 | A | 1/1963 | Mocarski |
| 3,109,588 | A | 11/1963 | Polhemus et al. |
| 3,121,228 | A | 2/1964 | Kalmus |
| 3,294,083 | A | 12/1966 | Alderson |
| 3,367,326 | A | 2/1968 | Frazier |
| 3,439,256 | A | 4/1969 | Robert |
| 3,519,436 | A | 7/1970 | Bauer et al. |
| 3,577,160 | A | 5/1971 | White |
| 3,600,625 | A | 8/1971 | Asahide et al. |
| 3,605,725 | A | 9/1971 | Bentov |
| 3,614,950 | A | 10/1971 | Graham |
| 3,644,825 | A | 2/1972 | Davis et al. |
| 3,674,014 | A | 7/1972 | Hans |
| 3,702,935 | A | 11/1972 | Carey et al. |
| 3,704,707 | A | 12/1972 | Halloran |
| 3,821,469 | A | 6/1974 | Whetstone et al. |
| 3,822,697 | A | 7/1974 | Komiya |
| 3,868,565 | A | 2/1975 | Kuipers |

(Continued)

FOREIGN PATENT DOCUMENTS

| | | |
|---|---|---|
| CA | 964149 A | 3/1975 |
| DE | 3042343 A1 | 6/1982 |

(Continued)

OTHER PUBLICATIONS

Partial European Search Report issued in corresponding European Application No. 18215857.6 dated Apr. 15, 2019.

(Continued)

*Primary Examiner* — Tu T Nguyen
(74) *Attorney, Agent, or Firm* — Weber Rosselli & Cannon LLP

(57) ABSTRACT

A registration method whereby a sensor-based approach is used to establish initial registration and whereby upon the commencement of navigating an endoscope, image-based registration methods are used in order to more accurately maintain the registration between the endoscope location and previously-acquired images. A six-degree-of-freedom location sensor is placed on the probe in order to reduce the number of previously-acquired images that must be compared to a real-time image obtained from the endoscope.

12 Claims, No Drawings

(56) References Cited

U.S. PATENT DOCUMENTS

| | | |
|---|---|---|
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,135,184 A | 1/1979 | Pruzick |
| 4,173,228 A | 11/1979 | Childress et al. |
| 4,182,312 A | 1/1980 | Mushabac |
| 4,202,349 A | 5/1980 | Jones |
| 4,228,799 A | 10/1980 | Anichkov et al. |
| 4,249,167 A | 2/1981 | Purinton et al. |
| 4,256,112 A | 3/1981 | David et al. |
| 4,262,306 A | 4/1981 | Renner |
| 4,287,809 A | 9/1981 | Egli et al. |
| 4,298,874 A | 11/1981 | Kuipers |
| 4,308,530 A | 12/1981 | Kip et al. |
| 4,314,251 A | 2/1982 | Raab |
| 4,317,078 A | 2/1982 | Weed et al. |
| 4,319,136 A | 3/1982 | Randolph |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,341,385 A | 7/1982 | Doyle et al. |
| 4,346,384 A | 8/1982 | Raab |
| 4,358,856 A | 11/1982 | Stivender et al. |
| 4,368,536 A | 1/1983 | Pfeiler |
| 4,394,831 A | 7/1983 | Egli et al. |
| 4,396,885 A | 8/1983 | Constant |
| 4,396,945 A | 8/1983 | Dimatteo et al. |
| 4,403,321 A | 9/1983 | Krueger |
| 4,418,422 A | 11/1983 | Richter et al. |
| 4,419,012 A | 12/1983 | Stephenson et al. |
| 4,422,041 A | 12/1983 | Lienau |
| 4,425,511 A | 1/1984 | Brosh |
| 4,431,005 A | 2/1984 | Mccormick |
| 4,447,224 A | 5/1984 | Decant, Jr. et al. |
| 4,447,462 A | 5/1984 | Tafuri et al. |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,586,491 A | 5/1986 | Carpenter |
| 4,587,975 A | 5/1986 | Salo et al. |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Hunter et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,686,695 A | 8/1987 | Macovski |
| 4,688,037 A | 8/1987 | Krieg |
| 4,696,544 A | 9/1987 | Costella |
| 4,697,595 A | 10/1987 | Breyer et al. |
| 4,701,049 A | 10/1987 | Beckman et al. |
| 4,704,602 A | 11/1987 | Asbrink |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,726,355 A | 2/1988 | Okada |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,784,117 A | 11/1988 | Miyazaki |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oeberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,250 A | 5/1989 | Rotier |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,912 A | 8/1990 | Langberg |
| 4,945,914 A | 8/1990 | Allen |
| 4,951,653 A | 8/1990 | Fry et al. |
| 4,955,891 A | 9/1990 | Carol |
| 4,961,422 A | 10/1990 | Alexander et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,047 A | 5/1991 | Schwab |
| 5,013,317 A | 5/1991 | Dean et al. |
| 5,016,639 A | 5/1991 | Allen |
| 5,017,139 A | 5/1991 | Mushabac |
| 5,023,102 A | 6/1991 | Given, Jr. |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| RE33,662 E | 8/1991 | Blair et al. |
| 5,042,486 A | 8/1991 | Pfeiler et al. |

(56) References Cited

U.S. PATENT DOCUMENTS

| | | |
|---|---|---|
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,070,462 A | 12/1991 | Chau |
| 5,078,140 A | 1/1992 | Kwoh |
| 5,079,699 A | 1/1992 | Tuy et al. |
| 5,082,286 A | 1/1992 | Ryan et al. |
| 5,086,401 A | 2/1992 | Glassman et al. |
| 5,088,928 A | 2/1992 | Chan |
| 5,094,241 A | 3/1992 | Allen |
| 5,097,839 A | 3/1992 | Allen |
| 5,098,426 A | 3/1992 | Alfred et al. |
| 5,099,845 A | 3/1992 | Besz et al. |
| 5,099,846 A | 3/1992 | Hardy |
| 5,104,393 A | 4/1992 | Isner et al. |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,127,408 A | 7/1992 | Parsons et al. |
| 5,129,654 A | 7/1992 | Bogner |
| 5,142,930 A | 9/1992 | Allen et al. |
| 5,143,076 A | 9/1992 | Hardy et al. |
| 5,152,277 A | 10/1992 | Honda et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,130 A | 1/1993 | Kaiya |
| 5,178,164 A | 1/1993 | Allen |
| 5,178,621 A | 1/1993 | Cook et al. |
| 5,186,174 A | 2/1993 | Schloendorff et al. |
| 5,187,475 A | 2/1993 | Wagener et al. |
| 5,188,126 A | 2/1993 | Fabian et al. |
| 5,188,368 A | 2/1993 | Ryan |
| 5,190,059 A | 3/1993 | Fabian et al. |
| 5,190,285 A | 3/1993 | Levy et al. |
| 5,193,106 A | 3/1993 | Desena |
| 5,196,928 A | 3/1993 | Karasawa et al. |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,203,337 A | 4/1993 | Feldman |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,262,722 A | 11/1993 | Hedengren et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,301,061 A | 4/1994 | Nakada et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,307,816 A | 5/1994 | Hashimoto et al. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,327,889 A | 7/1994 | Imran |
| 5,329,944 A | 7/1994 | Fabian et al. |
| 5,330,485 A | 7/1994 | Clayman et al. |
| 5,333,168 A | 7/1994 | Fernandes et al. |
| 5,341,807 A | 8/1994 | Nardella |
| 5,347,289 A | 9/1994 | Elhardt |
| 5,353,795 A | 10/1994 | Souza et al. |
| 5,353,800 A | 10/1994 | Pohndorf et al. |
| 5,353,807 A | 10/1994 | Demarco |
| 5,357,253 A | 10/1994 | Van et al. |
| 5,359,417 A | 10/1994 | Mueller et al. |
| 5,368,030 A | 11/1994 | Zinreich et al. |
| 5,371,778 A | 12/1994 | Yanof et al. |
| 5,375,596 A | 12/1994 | Twiss et al. |
| 5,376,795 A | 12/1994 | Hasegawa et al. |
| 5,377,678 A | 1/1995 | Dumoulin et al. |
| 5,383,454 A | 1/1995 | Bucholz et al. |
| 5,383,852 A | 1/1995 | Stevens-Wright et al. |
| 5,385,146 A | 1/1995 | Goldreyer |
| 5,385,148 A | 1/1995 | Lesh et al. |
| 5,386,828 A | 2/1995 | Owens et al. |
| 5,389,073 A | 2/1995 | Imran |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,321 A | 3/1995 | Houser et al. |
| 5,397,329 A | 3/1995 | Allen |
| 5,398,684 A | 3/1995 | Hardy |
| 5,398,691 A | 3/1995 | Martin et al. |
| 5,399,146 A | 3/1995 | Nowacki et al. |
| 5,400,384 A | 3/1995 | Fernandes et al. |
| 5,400,771 A | 3/1995 | Pirak et al. |
| 5,402,801 A | 4/1995 | Taylor |
| 5,405,346 A | 4/1995 | Grundy et al. |
| 5,408,409 A | 4/1995 | Glassman et al. |
| 5,409,000 A | 4/1995 | Imran |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'farrell et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| 5,435,573 A | 7/1995 | Oakford |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |

(56) References Cited

U.S. PATENT DOCUMENTS

| | | |
|---|---|---|
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,447,156 A | 9/1995 | Dumoulin et al. |
| 5,448,610 A | 9/1995 | Yamamoto et al. |
| 5,453,686 A | 9/1995 | Anderson |
| 5,456,254 A | 10/1995 | Pietroski et al. |
| 5,456,664 A | 10/1995 | Heinzelman et al. |
| 5,456,689 A | 10/1995 | Kresch et al. |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,472,441 A | 12/1995 | Edwards et al. |
| 5,476,100 A | 12/1995 | Galel |
| 5,476,495 A | 12/1995 | Kordis et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,489,256 A | 2/1996 | Adair |
| 5,490,196 A | 2/1996 | Rudich et al. |
| 5,492,131 A | 2/1996 | Galel |
| 5,492,713 A | 2/1996 | Sommermeyer |
| 5,493,517 A | 2/1996 | Frazier |
| 5,494,034 A | 2/1996 | Schloendorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,515,853 A | 5/1996 | Smith et al. |
| 5,517,990 A | 5/1996 | Kalfas et al. |
| 5,520,059 A | 5/1996 | Garshelis |
| 5,522,814 A | 6/1996 | Bernaz |
| 5,522,815 A | 6/1996 | Durgin, Jr. et al. |
| 5,531,227 A | 7/1996 | Bret |
| 5,531,520 A | 7/1996 | Grimson et al. |
| 5,531,686 A | 7/1996 | Lundquist et al. |
| 5,542,938 A | 8/1996 | Avellanet et al. |
| 5,543,951 A | 8/1996 | Moehrmann |
| 5,545,200 A | 8/1996 | West et al. |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Michael et al. |
| 5,555,883 A | 9/1996 | Avitall |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-Haim |
| 5,571,083 A | 11/1996 | Lemelson |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,577,991 A | 11/1996 | Akui et al. |
| 5,583,909 A | 12/1996 | Hanover et al. |
| 5,588,033 A | 12/1996 | Yeung |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,599,305 A | 2/1997 | Hermann et al. |
| 5,600,330 A | 2/1997 | Blood |
| 5,603,318 A | 2/1997 | Heilbrun et al. |
| 5,606,975 A | 3/1997 | Liang et al. |
| 5,611,025 A | 3/1997 | Lorensen et al. |
| 5,617,462 A | 4/1997 | Bruce |
| 5,617,857 A | 4/1997 | Chader et al. |
| 5,619,261 A | 4/1997 | Larry |
| 5,620,734 A | 4/1997 | Wesdorp et al. |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,634 A | 6/1997 | Kordis et al. |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Larry et al. |
| 5,643,175 A | 7/1997 | Adair |
| 5,643,268 A | 7/1997 | Vilsmeier et al. |
| 5,645,065 A | 7/1997 | Shapiro et al. |
| 5,646,524 A | 7/1997 | Gilboa |
| 5,646,525 A | 7/1997 | Gilboa |
| 5,647,361 A | 7/1997 | Damadian |
| 5,651,047 A | 7/1997 | Moorman et al. |
| 5,660,856 A | 8/1997 | Adler-Moore et al. |
| 5,662,108 A | 9/1997 | Budd et al. |
| 5,662,111 A | 9/1997 | Cosman |
| 5,664,001 A | 9/1997 | Tachibana et al. |
| 5,668,844 A | 9/1997 | Webber |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,696,500 A | 12/1997 | Diem |
| 5,697,377 A | 12/1997 | Wittkampf |
| 5,701,898 A | 12/1997 | Adam et al. |
| 5,702,406 A | 12/1997 | Vilsmeier et al. |
| 5,704,361 A | 1/1998 | Seward et al. |
| 5,711,299 A | 1/1998 | Manwaring et al. |
| 5,713,369 A | 2/1998 | Tao et al. |
| 5,713,853 A | 2/1998 | Clark et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Michael et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,740,808 A | 4/1998 | Panescu et al. |
| 5,741,214 A | 4/1998 | Ouchi et al. |
| 5,741,320 A | 4/1998 | Thornton et al. |
| 5,742,394 A | 4/1998 | Hansen |
| 5,744,802 A | 4/1998 | Muehllehner et al. |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,752,518 A | 5/1998 | Mcgee et al. |
| 5,755,725 A | 5/1998 | Druais |
| RE35,816 E | 6/1998 | Schulz |
| 5,758,667 A | 6/1998 | Slettenmark |
| 5,760,335 A | 6/1998 | Gilboa |
| 5,762,064 A | 6/1998 | Polvani |
| 5,767,699 A | 6/1998 | Bosnyak et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |

(56) References Cited

U.S. PATENT DOCUMENTS

| | | |
|---|---|---|
| 5,776,050 A | 7/1998 | Chen et al. |
| 5,776,064 A | 7/1998 | Kalfas et al. |
| 5,782,765 A | 7/1998 | Jonkman |
| 5,782,828 A | 7/1998 | Chen et al. |
| 5,787,886 A | 8/1998 | Kelly et al. |
| 5,792,055 A | 8/1998 | Mckinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'farrell et al. |
| 5,803,084 A | 9/1998 | Olson |
| 5,803,089 A | 9/1998 | Ferre et al. |
| 5,807,252 A | 9/1998 | Hassfeld et al. |
| 5,810,007 A | 9/1998 | Holupka et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,820,591 A | 10/1998 | Thompson et al. |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,837,001 A | 11/1998 | Mackey |
| 5,840,024 A | 11/1998 | Taniguchi et al. |
| 5,840,025 A | 11/1998 | Ben-Haim |
| 5,842,984 A | 12/1998 | Avitall |
| 5,843,051 A | 12/1998 | Adams et al. |
| 5,843,076 A | 12/1998 | Webster, Jr. et al. |
| 5,846,183 A | 12/1998 | Chilcoat |
| 5,848,967 A | 12/1998 | Cosman |
| 5,851,183 A | 12/1998 | Bucholz |
| 5,853,327 A | 12/1998 | Gilboa |
| 5,857,997 A | 1/1999 | Cimino et al. |
| 5,865,726 A | 2/1999 | Katsurada et al. |
| 5,865,846 A | 2/1999 | Bryan et al. |
| 5,868,673 A | 2/1999 | Vesely |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,871,523 A | 2/1999 | Fleischman et al. |
| 5,873,822 A | 2/1999 | Ferre et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,134 A | 4/1999 | Goble et al. |
| 5,891,157 A | 4/1999 | Day et al. |
| 5,893,885 A | 4/1999 | Webster, Jr. |
| 5,899,860 A | 5/1999 | Pfeiffer et al. |
| 5,902,239 A | 5/1999 | Buurman |
| 5,902,324 A | 5/1999 | Thompson et al. |
| 5,904,691 A | 5/1999 | Barnett et al. |
| 5,907,395 A | 5/1999 | Schulz et al. |
| 5,909,476 A | 6/1999 | Wang et al. |
| 5,913,820 A | 6/1999 | Bladen et al. |
| 5,916,210 A | 6/1999 | Winston |
| 5,919,147 A | 7/1999 | Jain |
| 5,919,188 A | 7/1999 | Shearon et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,930,329 A | 7/1999 | Navab |
| 5,935,160 A | 8/1999 | Auricchio et al. |
| 5,938,585 A | 8/1999 | Donofrio |
| 5,938,602 A | 8/1999 | Lloyd |
| 5,938,603 A | 8/1999 | Ponzi |
| 5,938,694 A | 8/1999 | Jaraczewski et al. |
| 5,941,251 A | 8/1999 | Panescu et al. |
| 5,944,023 A | 8/1999 | Johnson et al. |
| 5,947,925 A | 9/1999 | Ashiya et al. |
| 5,947,980 A | 9/1999 | Jensen et al. |
| 5,947,981 A | 9/1999 | Cosman |
| 5,950,629 A | 9/1999 | Taylor et al. |
| 5,951,461 A | 9/1999 | Nyo et al. |
| 5,951,475 A | 9/1999 | Gueziec et al. |
| 5,951,571 A | 9/1999 | Audette |
| 5,954,647 A | 9/1999 | Bova et al. |
| 5,954,649 A | 9/1999 | Chia et al. |
| 5,954,796 A | 9/1999 | Mccarty et al. |
| 5,957,844 A | 9/1999 | Dekel et al. |
| 5,966,090 A | 10/1999 | Mcewan |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,127 A | 11/1999 | Lax |
| 5,976,156 A | 11/1999 | Taylor et al. |
| 5,980,504 A | 11/1999 | Sharkey et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,004,269 A | 12/1999 | Crowley et al. |
| 6,006,126 A | 12/1999 | Cosman |
| 6,006,127 A | 12/1999 | Brug et al. |
| 6,013,087 A | 1/2000 | Adams et al. |
| 6,014,580 A | 1/2000 | Blume et al. |
| 6,016,439 A | 1/2000 | Acker |
| 6,019,724 A | 2/2000 | Gronningsaeter et al. |
| 6,019,725 A | 2/2000 | Vesely et al. |
| 6,019,728 A | 2/2000 | Iwata et al. |
| 6,022,578 A | 2/2000 | Miller |
| 6,024,695 A | 2/2000 | Taylor et al. |
| 6,024,739 A | 2/2000 | Ponzi et al. |
| 6,032,675 A | 3/2000 | Rubinsky |
| 6,035,229 A | 3/2000 | Silverstein et al. |
| 6,050,724 A | 4/2000 | Schmitz et al. |
| 6,059,718 A | 5/2000 | Taniguchi et al. |
| 6,061,588 A | 5/2000 | Thornton et al. |
| 6,063,022 A | 5/2000 | Ben-Haim |
| 6,064,390 A | 5/2000 | Sagar et al. |
| 6,071,288 A | 6/2000 | Carol et al. |
| 6,073,043 A | 6/2000 | Schneider |
| 6,076,008 A | 6/2000 | Bucholz |
| 6,077,257 A | 6/2000 | Edwards et al. |
| 6,096,036 A | 8/2000 | Bowe et al. |
| 6,096,050 A | 8/2000 | Audette |
| 6,104,294 A | 8/2000 | Andersson et al. |
| 6,104,944 A | 8/2000 | Martinelli |
| 6,106,517 A | 8/2000 | Zupkas |
| 6,112,111 A | 8/2000 | Glantz |
| 6,115,626 A | 9/2000 | Whayne et al. |
| 6,117,476 A | 9/2000 | Eger et al. |
| 6,118,845 A | 9/2000 | Simon et al. |
| 6,122,538 A | 9/2000 | Sliwa, Jr. et al. |
| 6,122,541 A | 9/2000 | Cosman et al. |
| 6,123,979 A | 9/2000 | Hepburn et al. |
| 6,131,396 A | 10/2000 | Duerr et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,171,303 B1 | 1/2001 | Ben-Haim et al. |
| 6,172,499 B1 | 1/2001 | Ashe |
| 6,175,756 B1 | 1/2001 | Ferre et al. |
| 6,178,345 B1 | 1/2001 | Vilsmeier et al. |

(56) References Cited

U.S. PATENT DOCUMENTS

| | | |
|---|---|---|
| 6,179,809 B1 | 1/2001 | Khairkhahan et al. |
| 6,183,444 B1 | 2/2001 | Glines et al. |
| 6,188,355 B1 | 2/2001 | Gilboa |
| 6,192,280 B1 | 2/2001 | Sommer et al. |
| 6,194,639 B1 | 2/2001 | Botella et al. |
| 6,201,387 B1 | 3/2001 | Govari |
| 6,203,493 B1 | 3/2001 | Ben-Haim |
| 6,203,497 B1 | 3/2001 | Dekel et al. |
| 6,208,884 B1 | 3/2001 | Kumar et al. |
| 6,210,362 B1 | 4/2001 | Ponzi |
| 6,211,666 B1 | 4/2001 | Acker |
| 6,213,995 B1 | 4/2001 | Steen et al. |
| 6,213,998 B1 | 4/2001 | Shen et al. |
| 6,216,027 B1 | 4/2001 | Parker et al. |
| 6,216,029 B1 | 4/2001 | Paltieli |
| 6,223,067 B1 | 4/2001 | Vilsmeier et al. |
| 6,226,543 B1 | 5/2001 | Gilboa et al. |
| 6,233,476 B1 | 5/2001 | Strommer et al. |
| 6,236,875 B1 | 5/2001 | Bucholz et al. |
| 6,245,020 B1 | 6/2001 | Moore et al. |
| 6,246,231 B1 | 6/2001 | Ashe |
| 6,246,784 B1 | 6/2001 | Summers et al. |
| 6,246,898 B1 | 6/2001 | Vesely et al. |
| 6,246,899 B1 | 6/2001 | Chia et al. |
| 6,248,074 B1 | 6/2001 | Ohno et al. |
| 6,253,770 B1 | 7/2001 | Acker et al. |
| 6,259,942 B1 | 7/2001 | Westermann et al. |
| 6,264,654 B1 | 7/2001 | Swartz et al. |
| 6,272,371 B1 | 8/2001 | Shlomo |
| 6,273,896 B1 | 8/2001 | Franck et al. |
| 6,285,902 B1 | 9/2001 | Kienzle et al. |
| 6,289,235 B1 | 9/2001 | Webber et al. |
| 6,298,262 B1 | 10/2001 | Franck et al. |
| 6,304,769 B1 | 10/2001 | Arenson et al. |
| 6,306,097 B1 | 10/2001 | Park et al. |
| 6,314,310 B1 | 11/2001 | Ben-Haim et al. |
| 6,319,250 B1 | 11/2001 | Falwell et al. |
| 6,331,116 B1 | 12/2001 | Kaufman et al. |
| 6,331,156 B1 | 12/2001 | Haefele et al. |
| 6,332,089 B1 | 12/2001 | Acker et al. |
| 6,335,617 B1 | 1/2002 | Osadchy et al. |
| 6,341,231 B1 | 1/2002 | Ferre et al. |
| 6,345,112 B1 | 2/2002 | Summers et al. |
| 6,346,940 B1 | 2/2002 | Fukunaga |
| 6,351,513 B1 | 2/2002 | Bani-Hashemi et al. |
| 6,351,659 B1 | 2/2002 | Vilsmeier |
| 6,366,799 B1 | 4/2002 | Acker et al. |
| 6,373,240 B1 | 4/2002 | Govari |
| 6,380,732 B1 | 4/2002 | Gilboa |
| 6,381,485 B1 | 4/2002 | Hunter et al. |
| 6,383,144 B1 | 5/2002 | Mooney et al. |
| 6,405,072 B1 | 6/2002 | Cosman |
| 6,423,009 B1 | 7/2002 | Downey et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,443,894 B1 | 9/2002 | Sumanaweera et al. |
| 6,445,943 B1 | 9/2002 | Ferre et al. |
| 6,447,504 B1 | 9/2002 | Ben-Haim et al. |
| 6,453,190 B1 | 9/2002 | Acker et al. |
| 6,468,265 B1 | 10/2002 | Evans et al. |
| 6,470,207 B1 | 10/2002 | Simon et al. |
| 6,473,635 B1 | 10/2002 | Rasche |
| 6,474,341 B1 | 11/2002 | Hunter et al. |
| 6,478,802 B2 | 11/2002 | Kienzle et al. |
| 6,484,049 B1 | 11/2002 | Seeley et al. |
| 6,484,118 B1 | 11/2002 | Govari |
| 6,490,475 B1 | 12/2002 | Seeley et al. |
| 6,493,573 B1 | 12/2002 | Martinelli et al. |
| 6,498,477 B1 | 12/2002 | Govari et al. |
| 6,498,944 B1 | 12/2002 | Ben-Haim et al. |
| 6,499,488 B1 | 12/2002 | Hunter et al. |
| 6,516,046 B1 | 2/2003 | Froehlich et al. |
| 6,517,534 B1 | 2/2003 | Mcgovern et al. |
| 6,527,443 B1 | 3/2003 | Vilsmeier et al. |
| 6,551,325 B2 | 4/2003 | Neubauer et al. |
| 6,556,696 B1 | 4/2003 | Summers et al. |
| 6,558,333 B2 | 5/2003 | Gilboa et al. |
| 6,574,492 B1 | 6/2003 | Ben-Haim et al. |
| 6,574,498 B1 | 6/2003 | Gilboa |
| 6,580,938 B1 | 6/2003 | Acker |
| 6,584,174 B2 | 6/2003 | Schubert et al. |
| 6,585,763 B1 | 7/2003 | Keilman et al. |
| 6,591,129 B1 | 7/2003 | Ben-Haim et al. |
| 6,593,884 B1 | 7/2003 | Gilboa et al. |
| 6,609,022 B2 | 8/2003 | Vilsmeier et al. |
| 6,611,700 B1 | 8/2003 | Vilsmeier et al. |
| 6,615,155 B2 | 9/2003 | Gilboa |
| 6,618,612 B1 | 9/2003 | Acker et al. |
| 6,628,980 B2 | 9/2003 | Atalar et al. |
| 6,640,128 B2 | 10/2003 | Vilsmeier et al. |
| 6,650,927 B1 | 11/2003 | Keidar |
| 6,666,864 B2 | 12/2003 | Bencini et al. |
| 6,676,659 B2 | 1/2004 | Hutchins et al. |
| 6,690,816 B2 | 2/2004 | Aylward et al. |
| 6,690,963 B2 | 2/2004 | Ben-Haim et al. |
| 6,694,162 B2 | 2/2004 | Hartlep |
| 6,701,179 B1 | 3/2004 | Martinelli et al. |
| 6,702,780 B1 | 3/2004 | Gilboa et al. |
| 6,706,041 B1 | 3/2004 | Costantino |
| 6,711,429 B1 | 3/2004 | Gilboa et al. |
| 6,735,465 B2 | 5/2004 | Panescu |
| 6,751,492 B2 | 6/2004 | Ben-Haim |
| 6,770,070 B1 | 8/2004 | Balbierz |
| 6,788,967 B2 | 9/2004 | Ben-Haim et al. |
| 6,796,963 B2 | 9/2004 | Carpenter et al. |
| 6,810,281 B2 | 10/2004 | Brock et al. |
| 6,833,814 B2 | 12/2004 | Gilboa et al. |
| 6,887,236 B2 | 5/2005 | Gilboa |
| 6,947,788 B2 | 9/2005 | Gilboa et al. |
| 6,976,013 B1 | 12/2005 | Mah |
| 6,995,729 B2 | 2/2006 | Govari et al. |
| 6,996,430 B1 | 2/2006 | Gilboa et al. |
| 7,033,325 B1 | 4/2006 | Sullivan |
| 7,176,936 B2 | 2/2007 | Sauer et al. |
| 7,197,354 B2 | 3/2007 | Sobe |
| 7,233,820 B2 | 6/2007 | Gilboa |
| 7,236,567 B2 | 6/2007 | Sandkamp et al. |
| 7,286,868 B2 | 10/2007 | Govari |
| 7,301,332 B2 | 11/2007 | Govari et al. |
| 7,321,228 B2 | 1/2008 | Govari |
| 7,324,915 B2 | 1/2008 | Altmann et al. |
| 7,343,195 B2 | 3/2008 | Strommer et al. |
| 7,353,125 B2 | 4/2008 | Nieminen et al. |
| 7,357,795 B2 | 4/2008 | Kaji et al. |
| 7,366,562 B2 | 4/2008 | Dukesherer et al. |
| 7,370,656 B2 | 5/2008 | Gleich et al. |
| 7,373,271 B1 | 5/2008 | Schneider |
| 7,386,339 B2 | 6/2008 | Strommer et al. |
| 7,397,364 B2 | 7/2008 | Govari |
| 7,399,296 B2 | 7/2008 | Poole et al. |
| 7,420,468 B2 | 9/2008 | Fabian et al. |
| 7,497,029 B2 | 3/2009 | Plassky et al. |
| 7,505,809 B2 | 3/2009 | Strommer et al. |
| 7,517,318 B2 | 4/2009 | Altmann et al. |
| 7,517,319 B2 | 4/2009 | Kushnir et al. |
| 7,536,218 B2 | 5/2009 | Govari et al. |
| 7,555,330 B2 | 6/2009 | Gilboa et al. |
| RE40,852 E | 7/2009 | Martinelli et al. |
| 7,570,987 B2 | 8/2009 | Raabe et al. |
| 7,577,474 B2 | 8/2009 | Vilsmeier |
| 7,579,837 B2 | 8/2009 | Fath et al. |
| 7,587,235 B2 | 9/2009 | Wist et al. |
| 7,599,535 B2 | 10/2009 | Kiraly et al. |
| 7,599,810 B2 | 10/2009 | Yamazaki |
| 7,604,601 B2 | 10/2009 | Altmann et al. |
| 7,630,753 B2 | 12/2009 | Simon et al. |
| 7,634,122 B2 | 12/2009 | Bertram et al. |
| 7,636,595 B2 | 12/2009 | Marquart et al. |
| 7,641,609 B2 | 1/2010 | Ohnishi et al. |
| 7,652,468 B2 | 1/2010 | Kruger et al. |
| 7,652,578 B2 | 1/2010 | Braun et al. |

(56) References Cited

U.S. PATENT DOCUMENTS

| | | |
|---|---|---|
| 7,657,300 B2 | 2/2010 | Hunter et al. |
| 7,659,912 B2 | 2/2010 | Akimoto et al. |
| 7,660,623 B2 | 2/2010 | Hunter et al. |
| 7,680,528 B2 | 3/2010 | Pfister et al. |
| 7,684,849 B2 | 3/2010 | Wright et al. |
| 7,686,767 B2 | 3/2010 | Maschke |
| 7,688,064 B2 | 3/2010 | Shalgi et al. |
| 7,696,899 B2 | 4/2010 | Immerz et al. |
| 7,697,972 B2 | 4/2010 | Verard et al. |
| 7,697,973 B2 | 4/2010 | Strommer et al. |
| 7,697,974 B2 | 4/2010 | Jenkins et al. |
| 7,720,517 B2 | 5/2010 | Drysen |
| 7,722,565 B2 | 5/2010 | Wood et al. |
| 7,725,154 B2 | 5/2010 | Beck et al. |
| 7,725,164 B2 | 5/2010 | Suurmond et al. |
| 7,727,269 B2 | 6/2010 | Abraham-Fuchs et al. |
| 7,729,742 B2 | 6/2010 | Govari |
| 7,744,605 B2 | 6/2010 | Vilsmeier et al. |
| 7,747,307 B2 | 6/2010 | Wright et al. |
| 7,751,865 B2 | 7/2010 | Jascob et al. |
| 7,782,189 B2 | 8/2010 | Spoonhower et al. |
| 7,784,468 B2 | 8/2010 | Fabian et al. |
| 7,831,076 B2 | 11/2010 | Altmann et al. |
| 7,912,662 B2 | 3/2011 | Zuhars et al. |
| 7,969,143 B2 | 6/2011 | Gilboa |
| 7,996,060 B2 | 8/2011 | Trofimov et al. |
| 8,452,068 B2 | 5/2013 | Averbuch et al. |
| 2001/0007918 A1 | 7/2001 | Vilsmeier et al. |
| 2001/0031919 A1 | 10/2001 | Strommer et al. |
| 2001/0034530 A1 | 10/2001 | Malackowski et al. |
| 2001/0036245 A1 | 11/2001 | Kienzle et al. |
| 2001/0038705 A1 | 11/2001 | Rubbert et al. |
| 2002/0022837 A1 | 2/2002 | Mazzocchi et al. |
| 2002/0045916 A1 | 4/2002 | Gray et al. |
| 2002/0045919 A1 | 4/2002 | Johansson-Ruden et al. |
| 2002/0065461 A1 | 5/2002 | Cosman |
| 2002/0082498 A1 | 6/2002 | Wendt et al. |
| 2002/0095081 A1 | 7/2002 | Vilsmeier |
| 2002/0128565 A1 | 9/2002 | Rudy |
| 2002/0137014 A1 | 9/2002 | Anderson et al. |
| 2002/0143324 A1 | 10/2002 | Edwards |
| 2002/0165448 A1 | 11/2002 | Ben-Haim et al. |
| 2002/0173689 A1 | 11/2002 | Kaplan |
| 2002/0193686 A1 | 12/2002 | Gilboa |
| 2003/0018251 A1 | 1/2003 | Solomon |
| 2003/0074011 A1 | 4/2003 | Gilboa et al. |
| 2003/0086599 A1 | 5/2003 | Armato et al. |
| 2003/0099390 A1 | 5/2003 | Zeng et al. |
| 2003/0142753 A1 | 7/2003 | Gunday |
| 2003/0144658 A1 | 7/2003 | Schwartz et al. |
| 2003/0160721 A1 | 8/2003 | Gilboa et al. |
| 2003/0197686 A1 | 10/2003 | Usuda |
| 2003/0216639 A1 | 11/2003 | Gilboa et al. |
| 2004/0000249 A1 | 1/2004 | Avetisian |
| 2004/0006268 A1 | 1/2004 | Gilboa et al. |
| 2004/0015049 A1 | 1/2004 | Zaar |
| 2004/0019350 A1 | 1/2004 | O'brien et al. |
| 2004/0024309 A1 | 2/2004 | Ferre et al. |
| 2004/0086161 A1 | 5/2004 | Sivaramakrishna et al. |
| 2004/0097804 A1 | 5/2004 | Sobe |
| 2004/0122310 A1 | 6/2004 | Lim |
| 2004/0138548 A1 | 7/2004 | Strommer et al. |
| 2004/0143317 A1 | 7/2004 | Stinson et al. |
| 2004/0169509 A1 | 9/2004 | Czipott et al. |
| 2004/0215181 A1 | 10/2004 | Christopherson et al. |
| 2004/0249267 A1 | 12/2004 | Gilboa |
| 2004/0254454 A1 | 12/2004 | Kockro |
| 2005/0018885 A1 | 1/2005 | Chen et al. |
| 2005/0027193 A1 | 2/2005 | Mitschke et al. |
| 2005/0033149 A1 | 2/2005 | Strommer et al. |
| 2005/0059890 A1 | 3/2005 | Deal et al. |
| 2005/0085715 A1 | 4/2005 | Dukesherer et al. |
| 2005/0090818 A1 | 4/2005 | Pike, Jr. et al. |
| 2005/0107688 A1 | 5/2005 | Strommer |
| 2005/0119527 A1 | 6/2005 | Banik et al. |
| 2005/0154282 A1 | 7/2005 | Li et al. |
| 2005/0182295 A1 | 8/2005 | Soper et al. |
| 2005/0197566 A1 | 9/2005 | Strommer et al. |
| 2005/0272971 A1 | 12/2005 | Ohnishi et al. |
| 2006/0015126 A1 | 1/2006 | Sher |
| 2006/0058647 A1 | 3/2006 | Strommer et al. |
| 2006/0064006 A1 | 3/2006 | Strommer et al. |
| 2006/0079759 A1 | 4/2006 | Vaillant et al. |
| 2006/0116575 A1 | 6/2006 | Willis |
| 2006/0149134 A1 | 7/2006 | Soper et al. |
| 2006/0241396 A1 | 10/2006 | Fabian et al. |
| 2006/0241399 A1 | 10/2006 | Fabian |
| 2007/0078334 A1 | 4/2007 | Scully et al. |
| 2007/0163597 A1 | 7/2007 | Mikkaichi et al. |
| 2007/0167714 A1 | 7/2007 | Kiraly et al. |
| 2007/0167738 A1 | 7/2007 | Timinger et al. |
| 2007/0167743 A1 | 7/2007 | Honda et al. |
| 2007/0167801 A1* | 7/2007 | Webler .................. G06T 19/00 600/459 |
| 2007/0167804 A1 | 7/2007 | Park et al. |
| 2007/0167806 A1 | 7/2007 | Wood et al. |
| 2007/0225553 A1 | 9/2007 | Shahidi |
| 2007/0232882 A1 | 10/2007 | Glossop et al. |
| 2007/0232898 A1 | 10/2007 | Huynh et al. |
| 2007/0265639 A1 | 11/2007 | Danek et al. |
| 2007/0287901 A1 | 12/2007 | Strommer et al. |
| 2008/0008367 A1 | 1/2008 | Franaszek et al. |
| 2008/0008368 A1 | 1/2008 | Matsumoto |
| 2008/0018468 A1 | 1/2008 | Volpi et al. |
| 2008/0033452 A1 | 2/2008 | Vetter et al. |
| 2008/0086051 A1 | 4/2008 | Voegele |
| 2008/0097154 A1 | 4/2008 | Makower et al. |
| 2008/0097187 A1 | 4/2008 | Gielen et al. |
| 2008/0118135 A1 | 5/2008 | Averbuch et al. |
| 2008/0132909 A1 | 6/2008 | Jascob et al. |
| 2008/0132911 A1 | 6/2008 | Sobe |
| 2008/0139886 A1 | 6/2008 | Tatsuyama |
| 2008/0139915 A1 | 6/2008 | Dolan et al. |
| 2008/0144909 A1 | 6/2008 | Wiemker et al. |
| 2008/0147000 A1 | 6/2008 | Seibel et al. |
| 2008/0154172 A1 | 6/2008 | Mauch |
| 2008/0157755 A1 | 7/2008 | Kruger et al. |
| 2008/0161682 A1 | 7/2008 | Kendrick et al. |
| 2008/0162074 A1 | 7/2008 | Schneider |
| 2008/0183071 A1 | 7/2008 | Strommer et al. |
| 2008/0188749 A1 | 8/2008 | Rasche et al. |
| 2008/0212881 A1 | 9/2008 | Hirakawa |
| 2008/0247622 A1 | 10/2008 | Aylward et al. |
| 2009/0082665 A1 | 3/2009 | Anderson |
| 2009/0182224 A1 | 7/2009 | Shmarak et al. |
| 2009/0189820 A1 | 7/2009 | Saito et al. |
| 2009/0318797 A1 | 12/2009 | Hadani |
| 2010/0016658 A1 | 1/2010 | Zou et al. |
| 2011/0085720 A1 | 4/2011 | Averbuch |

FOREIGN PATENT DOCUMENTS

| | | |
|---|---|---|
| DE | 3508730 A1 | 9/1986 |
| DE | 3520782 A1 | 12/1986 |
| DE | 3717871 A1 | 12/1988 |
| DE | 3831278 A1 | 3/1989 |
| DE | 3838011 A1 | 7/1989 |
| DE | 4213426 A1 | 10/1992 |
| DE | 4225112 C1 | 12/1993 |
| DE | 4233978 C1 | 4/1994 |
| DE | 19715202 A1 | 10/1998 |
| DE | 19751761 A1 | 10/1998 |
| DE | 19832296 A1 | 2/1999 |
| DE | 19747427 A1 | 5/1999 |
| DE | 10085137 T | 7/2010 |
| EP | 0062941 A1 | 10/1982 |
| EP | 0119660 A1 | 9/1984 |
| EP | 0155857 A2 | 9/1985 |
| EP | 0319844 A1 | 6/1989 |
| EP | 0326768 A2 | 8/1989 |
| EP | 0350996 A1 | 1/1990 |
| EP | 0419729 A1 | 4/1991 |
| EP | 0427358 A1 | 5/1991 |
| EP | 0456103 A2 | 11/1991 |

(56) References Cited

FOREIGN PATENT DOCUMENTS

| | | | | |
|---|---|---|---|---|
| EP | 0581704 | A1 | 2/1994 | |
| EP | 0600610 | A2 | 6/1994 | |
| EP | 0651968 | A1 | 5/1995 | |
| EP | 0655138 | A1 | 5/1995 | |
| EP | 0796633 | A1 | 9/1997 | |
| EP | 0829229 | A1 | 3/1998 | |
| EP | 0857461 | A2 | 8/1998 | |
| EP | 0894473 | A2 | 2/1999 | |
| EP | 0908146 | A2 | 4/1999 | |
| EP | 0922966 | A2 | 6/1999 | |
| EP | 0930046 | A2 | 7/1999 | |
| EP | 1078644 | A1 | 2/2001 | |
| EP | 2096523 | A1 | 9/2009 | |
| EP | 2117436 | A2 | 11/2009 | |
| EP | 1499235 | B1 | 8/2016 | |
| EP | 1499235 | B1 * | 8/2016 | ......... A61B 1/00154 |
| FR | 2417970 | A1 | 9/1979 | |
| FR | 2618211 | A1 | 1/1989 | |
| GB | 2094590 | A | 9/1982 | |
| GB | 2164856 | A | 4/1986 | |
| GB | 2197078 | A | 5/1988 | |
| JP | S63240851 | A | 10/1988 | |
| JP | H03267054 | A | 11/1991 | |
| JP | H06194639 | A | 7/1994 | |
| JP | H07159378 | A | 6/1995 | |
| JP | H08233601 | A | 9/1996 | |
| JP | H08299305 | A | 11/1996 | |
| JP | H0325752 | B | 11/1997 | |
| WO | 8809151 | A1 | 12/1988 | |
| WO | 8905123 | A1 | 6/1989 | |
| WO | 9005494 | A1 | 5/1990 | |
| WO | 9103982 | A1 | 4/1991 | |
| WO | 9104711 | A1 | 4/1991 | |
| WO | 9107726 | A1 | 5/1991 | |
| WO | 9203090 | A1 | 3/1992 | |
| WO | 9206645 | A1 | 4/1992 | |
| WO | 9404938 | A1 | 3/1994 | |
| WO | 9423647 | A1 | 10/1994 | |
| WO | 9424933 | A1 | 11/1994 | |
| WO | 9507055 | A1 | 3/1995 | |
| WO | 9509562 | A1 | 4/1995 | |
| WO | 9605768 | A1 | 2/1996 | |
| WO | 9611624 | A2 | 4/1996 | |
| WO | 9625882 | A1 | 8/1996 | |
| WO | 9632059 | A1 | 10/1996 | |
| WO | 9641119 | A1 | 12/1996 | |
| WO | 9700011 | A1 | 1/1997 | |
| WO | 9700054 | A1 | 1/1997 | |
| WO | 9700058 | A1 | 1/1997 | |
| WO | 9700059 | A1 | 1/1997 | |
| WO | 9700308 | A1 | 1/1997 | |
| WO | 9702650 | A1 | 1/1997 | |
| WO | 9724983 | A2 | 7/1997 | |
| WO | 9725101 | A2 | 7/1997 | |
| WO | 9729682 | A1 | 8/1997 | |
| WO | 9729684 | A1 | 8/1997 | |
| WO | 9729685 | A1 | 8/1997 | |
| WO | 9729701 | A1 | 8/1997 | |
| WO | 9729709 | A1 | 8/1997 | |
| WO | 9736143 | A1 | 10/1997 | |
| WO | 9736192 | A1 | 10/1997 | |
| WO | 9742517 | A1 | 11/1997 | |
| WO | 9744089 | A1 | 11/1997 | |
| WO | 9749453 | A1 | 12/1997 | |
| WO | 9800034 | A2 | 1/1998 | |
| WO | 9808554 | A1 | 3/1998 | |
| WO | 9811840 | A1 | 3/1998 | |
| WO | 9829032 | A1 | 7/1998 | |
| WO | 9835720 | A2 | 8/1998 | |
| WO | 9838908 | A1 | 9/1998 | |
| WO | 9848722 | A1 | 11/1998 | |
| WO | 9915097 | A2 | 4/1999 | |
| WO | 9916350 | A1 | 4/1999 | |
| WO | 9921498 | A1 | 5/1999 | |
| WO | 9923956 | A1 | 5/1999 | |
| WO | 9926549 | A1 | 6/1999 | |
| WO | 9926826 | A2 | 6/1999 | |
| WO | 9927839 | A2 | 6/1999 | |
| WO | 9929253 | A1 | 6/1999 | |
| WO | 9930777 | A1 | 6/1999 | |
| WO | 9932033 | A1 | 7/1999 | |
| WO | 9933406 | A1 | 7/1999 | |
| WO | 9937208 | A1 | 7/1999 | |
| WO | 9938449 | A1 | 8/1999 | |
| WO | 9952094 | A1 | 10/1999 | |
| WO | 9955415 | A1 | 11/1999 | |
| WO | 9960939 | A1 | 12/1999 | |
| WO | 0006701 | A1 | 2/2000 | |
| WO | 0010456 | A1 | 3/2000 | |
| WO | 0016684 | A1 | 3/2000 | |
| WO | 0035531 | A1 | 6/2000 | |
| WO | 0106917 | A1 | 2/2001 | |
| WO | 0112057 | A1 | 2/2001 | |
| WO | 0130437 | A1 | 5/2001 | |
| WO | 0167035 | A1 | 9/2001 | |
| WO | 0187136 | A2 | 11/2001 | |
| WO | 0191842 | A1 | 12/2001 | |
| WO | 02064011 | A2 | 8/2002 | |
| WO | 02070047 | A1 | 9/2002 | |
| WO | 03086498 | A2 | 10/2003 | |
| WO | 2004023986 | A1 | 3/2004 | |
| WO | 2006116597 | A2 | 11/2006 | |
| WO | 2008111070 | A2 | 9/2008 | |

OTHER PUBLICATIONS

United States Patent and Trademark Office, Final Office Action dated Dec. 17, 2010 in U.S. Appl. No. 12/723,577, 8 pages.
United States Patent and Trademark Office, Final Office Action dated Dec. 31, 2007 in U.S. Appl. No. 10/129,365, 7 pages.
United States Patent and Trademark Office, Final Office Action dated Jan. 14, 2009 in U.S. Appl. No. 10/190,847, 12 pages.
United States Patent and Trademark Office, Final Office Action dated Jan. 23, 2009 in U.S. Appl. No. 10/169,186, 9 pages.
United States Patent and Trademark Office, Final Office Action dated Jul. 14, 2006 in U.S. Appl. No. 10/129,365, 8 pages.
United States Patent and Trademark Office, Final Office Action dated Jul. 27, 2011 in U.S. Appl. No. 12/723,577, 12 pages.
United States Patent and Trademark Office, Final Office Action dated Jun. 24, 2008 in U.S. Appl. No. 10/258,124, 11 pages.
United States Patent and Trademark Office, Final Office Action dated Mar. 29, 2005 in U.S. Appl. No. 09/959,837, 4 pages.
United States Patent and Trademark Office, Final Office Action dated May 1, 2012 in U.S. Appl. No. 12/476,976, 6 pages.
United States Patent and Trademark Office, Final Office Action dated Nov. 22, 2011 in U.S. Appl. No. 12/417,381, 21 pages.
United States Patent and Trademark Office, Final Office Action dated Nov. 29, 2006 in U.S. Appl. No. 10/258,124, 11 pages.
United States Patent and Trademark Office, Final Office Action dated Nov. 4, 2011 in U.S. Appl. No. 11/393,537, 22 pages.
United States Patent and Trademark Office, Final Office Action dated Oct. 11, 2007 in U.S. Appl. No. 10/190,847, 13 pages.
United States Patent and Trademark Office, Final Office Action dated Oct. 5, 2007 in U.S. Appl. No. 10/169,186, 9 pages.
United States Patent and Trademark Office, Final Office Action dated Sep. 23, 2011 in U.S. Appl. No. 12/723,577, 12 pages.
United States Patent and Trademark Office, Notice of Allowance dated Apr. 6, 2011 in U.S. Appl. No. 11/765,330, 9 pages.
United States Patent and Trademark Office, Notice of Allowance dated Feb. 25, 2009 in U.S. Appl. No. 10/408,123, 8 pages.
United States Patent and Trademark Office, Notice of Allowance dated Jan. 3, 2005 in U.S. Appl. No. 09/879,109, 6 pages.
United States Patent and Trademark Office, Notice of Allowance dated Jan. 3, 2005 in U.S. Appl. No. 10/137,415, 10 pages.
United States Patent and Trademark Office, Notice of Allowance dated Mar. 19, 2012 in U.S. Appl. No. 12/478,573, 12 pages.
United States Patent and Trademark Office, Notice of Allowance dated Mar. 22, 2012 in U.S. Appl. No. 12/466,238, 11 pages.

(56) References Cited

OTHER PUBLICATIONS

United States Patent and Trademark Office, Notice of Allowance dated Mar. 26, 2002 in U.S. Appl. No. 09/860,484, 6 pages.
United States Patent and Trademark Office, Notice of Allowance dated Oct. 6, 2006 in U.S. Appl. No. 10/491,099, 9 pages.
United States Patent and Trademark Office, Office Action dated Apr. 1, 2011 in U.S. Appl. No. 11/393,537, 21 pages.
United States Patent and Trademark Office, Office Action dated Apr. 22, 2005 in U.S. Appl. No. 10/491,099, 5 pages.
United States Patent and Trademark Office, Office Action dated Apr. 29, 2011 in U.S. Appl. No. 12/417,381, 12 pages.
United States Patent and Trademark Office, Office Action dated Aug. 4, 2006 in U.S. Appl. No. 10/190,847, 7 pages.
United States Patent and Trademark Office, Office Action dated Dec. 1, 2005 in U.S. Appl. No. 10/258,124, 12 pages.
United States Patent and Trademark Office, Office Action dated Dec. 13, 2005 in U.S. Appl. No. 10/129,365, 7 pages.
United States Patent and Trademark Office, Office Action dated Dec. 15, 2011 in U.S. Appl. No. 12/170,385, 19 pages.
United States Patent and Trademark Office, Office Action dated Dec. 30, 2005 in U.S. Appl. No. 10/491,099, 15 pages.
United States Patent and Trademark Office, Office Action dated Dec. 31, 2009 in U.S. Appl. No. 11/427,353, 9 pages.
United States Patent and Trademark Office, Office Action dated Dec. 4, 2006 in U.S. Appl. No. 10/169,186, 9 pages.
United States Patent and Trademark Office, Office Action dated Feb. 16, 2011 in U.S. Appl. No. 12/723,577, 8 pages.
United States Patent and Trademark Office, Office Action dated Feb. 24, 2005 in U.S. Appl. No. 09/879,107, 6 pages.
United States Patent and Trademark Office, Office Action dated Jan. 16, 2002 in U.S. Appl. No. 09/860,484, 7 pages.
United States Patent and Trademark Office, Office Action dated Jan. 21, 2004 in U.S. Appl. No. 09/959,837, 8 pages.
United States Patent and Trademark Office, Office Action dated Jan. 22, 2009 in U.S. Appl. No. 11/427,353, 8 pages.
United States Patent and Trademark Office, Office Action dated Jul. 1, 2004 in U.S. Appl. No. 10/137,415, 14 pages.
United States Patent and Trademark Office, Office Action dated Jul. 11, 2007 in U.S. Appl. No. 10/258,124, 10 pages.
United States Patent and Trademark Office, Office Action dated Jul. 27, 2007 in U.S. Appl. No. 10/408,123, 6 pages.
United States Patent and Trademark Office, Office Action dated Jun. 24, 2009 in U.S. Appl. No. 10/129,365, 5 pages.
United States Patent and Trademark Office, Office Action dated Mar. 18, 2011 in U.S. Appl. No. 12/369,466, 13 pages.
United States Patent and Trademark Office, Office Action dated Mar. 26, 2007 in U.S. Appl. No. 10/190,847, 5 pages.
United States Patent and Trademark Office, Office Action dated Mar. 29, 2012 in U.S. Appl. No. 12/723,577, 11 pages.
United States Patent and Trademark Office, Office Action dated Mar. 31, 2011 in U.S. Appl. No. 12/490,237, 7 pages.
United States Patent and Trademark Office, Office Action dated Mar. 5, 2012 in U.S. Appl. No. 11/568,260, 12 pages.
United States Patent and Trademark Office, Office Action dated May 13, 2008 in U.S. Appl. No. 10/408,123, 6 pages.
United States Patent and Trademark Office, Office Action dated May 15, 2008 in U.S. Appl. No. 10/169,186, 9 pages.
United States Patent and Trademark Office, Office Action dated May 15, 2008 in U.S. Appl. No. 10/190,847, 13 pages.
United States Patent and Trademark Office, Office Action dated May 19, 2010 in U.S. Appl. No. 12/503,045, 12 pages.
United States Patent and Trademark Office, Office Action dated Nov. 13, 2002 in U.S. Appl. No. 09/463,177, 5 pages.
United States Patent and Trademark Office, Office Action dated Nov. 13, 2008 in U.S. Appl. No. 10/258,124, 13 pages.
United States Patent and Trademark Office, Office Action dated Nov. 15, 2010 in U.S. Appl. No. 12/490,237, 8 pages.
United States Patent and Trademark Office, Office Action dated Nov. 18, 2011 in U.S. Appl. No. 12/476,976, 6 pages.
United States Patent and Trademark Office, Office Action dated Nov. 2, 2011 in U.S. Appl. No. 12/478,573, 11 pages.
United States Patent and Trademark Office, Office Action dated Nov. 26, 2004 in U.S. Appl. No. 09/959,837, 8 pages.
United States Patent and Trademark Office, Office Action dated Nov. 4, 2008 in U.S. Appl. No. 10/129,365, 7 pages.
United States Patent and Trademark Office, Office Action dated Oct. 18, 2010 in U.S. Appl. No. 11/765,330, 35 pages.
United States Patent and Trademark Office, Office Action dated Oct. 22, 2010 in U.S. Appl. No. 12/723,577, 7 pages.
United States Patent and Trademark Office, Office Action dated Sep. 21, 2006 in U.S. Appl. No. 10/408,123, 9 pages.
United States Patent and Trademark Office, Office Action dated Sep. 6, 2002 in U.S. Appl. No. 09/463,177, 8 pages.
United States Patent and Trademark Office, Office Action dated Sep. 7, 2011 in U.S. Appl. No. 12/466,238, 14 pages.
WIPO, IB International Search Authority, International Search Report dated Jul. 14, 2009 in International Patent Application No. PCT/IB2009/000238, 1 page.
WIPO, U.S. International Preliminary Examining Authority, International Preliminary Examination Report dated Aug. 7, 2002 in International Patent Application No. PCT/US1999/026826, 4 pages.
WIPO, U.S. International Preliminary Examining Authority, International Preliminary Report on Patentability dated Aug. 9, 2001 in International Patent Application No. PCT/IS2000/026322, 4 pages.
WIPO, U.S. International Preliminary Examining Authority, International Preliminary Report on Patentability dated Dec. 6, 2010 in International Patent Application No. PCT/IL2009/000569, 6 pages.
WIPO, U.S. International Preliminary Examining Authority, International Preliminary Report on Patentability dated Jul. 19, 2006 in International Patent Application No. PCT/IL2005/000724, 4 pages.
WIPO, U.S. International Preliminary Examining Authority, International Preliminary Report on Patentability dated May 10, 2010 in International Patent Application No. PCT/I92009/005167, 5 pages.
WIPO, U.S. International Preliminary Examining Authority, International Preliminary Report on Patentability dated Sep. 29, 2011 in International Patent Application No. PCT/US2010/027544, 5 pages.
WIPO, U.S. International Search Authority, International Search Report and Written Opinion dated Jul. 12, 2006 in International Patent Application No. PCT/IB2011/000243, 7 pages.
WIPO, U.S. International Search Authority, International Search Report and Written Opinion dated Nov. 13, 2008 in International Patent Application No. PCT/US07/004567, 8 pages.
WIPO, U.S. International Search Authority, International Search Report and Written Opinion dated Oct. 26, 2009 in International Patent Application No. PCT/IB2009/005609, 11 pages.
WIPO, U.S. International Search Authority, International Search Report and Written Opinion dated Sep. 22, 2009 in International Patent Application No. PCT/IL2009/000553, 7 pages.
WIPO, U.S. International Search Authority, International Search Report and Written Opinion dated Sep. 24, 2009 in International Patent Application No. PCT/IL2009/000569, 7 pages.
WIPO, U.S. International Search Authority, International Search Report and Written Opinion dated Sep. 25, 2009 in International Patent Application No. PCT/IB2009/005167, 5 pages.
WIPO, U.S. International Search Authority, International Search Report dated Aug. 14, 2001 in International Patent Application No. PCT/IL2001/000224, 3 pages.
WIPO, U.S. International Search Authority, International Search Report dated Feb. 10, 2000 in International Patent Application No. PCT/IL1999/000371, 1 page.
Wipo, U.S. International Search Authority, International Search Report dated Feb. 13, 2002 in International Patent Application No. PCT/IL2001/000415, 2 pages.
WIPO, U.S. International Search Authority, International Search Report dated Feb. 23, 2000 in International Patent No. PCT/US1999/026095, 1 page.
WIPO, U.S. International Search Authority, International Search Report dated Feb. 23, 2001 in International Patent Application No. PCT/IL2000/00537, 3 pages.
WIPO, U.S. International Search Authority, International Search Report dated Jan. 3, 2002 in International Patent Application No. PCT/IL2001/000363, 2 pages.

(56) References Cited

OTHER PUBLICATIONS

WIPO, U.S. International Search Authority, International Search Report dated Jul. 31, 2002 in International Patent Application No. PCT/US2002/013317, 1 page.
WIPO, U.S. International Search Authority, International Search Report dated Jun. 27, 2001 in International Patent Application No. PCT/IL2001/000024, 7 pages.
WIPO, U.S. International Search Authority, International Search Report dated Mar. 14, 2006 in International Patent Application No. PCT/IL2005/000724, 1 page.
WIPO, U.S. International Search Authority, International Search Report dated Mar. 30, 2006 in International Patent Application No. PCT/IL2005/000452, 1 page.
WIPO, U.S. International Search Authority, International Search Report dated Mar. 31, 2000 in International Patent Application No. PCT/US1999/026826, 1 page.
WIPO, U.S. International Search Authority, International Search Report dated May 17, 2010 in International Patent Application No. PCT/US2010/027544, 2 pages.
WIPO, U.S. International Search Authority, International Search Report dated Nov. 16, 2001 in International Patent Application No. PCT/IL2000/000735, 1 page.
WIPO, U.S. International Search Authority, International Search Report dated Nov. 27, 2000 in International Patent Application No. PCT/US2000/021669, 1 page.
WIPO, U.S. International Search Authority, International Search Report dated Nov. 28, 2000 in International Patent Application No. PCT/US2000/026322, 1 page.
WIPO, U.S. International Search Authority, International Search Report dated Sep. 3, 1997 in International Patent Application No. PCT/IL1997/000054, 1 page.
WIPO, U.S. International Search Authority, Written Opinion dated May 17, 2010 in International Patent Application No. PCT/US2010/027544, 3 pages.
Breyer, B. et al., "Ultrasonically marked catheter—a method for positive echographic catheter position identification," Medical & Biological Engineering & Computing, May 1984, 22(3)268-271, 4 pages.
European Examination Reqport issued in Appl. No. EP 09 758 027.8 dated Feb. 21, 2018 (7 pages).
European Patent Office, Examination Report dated Apr. 15, 2005 in European Patent Application No. EP99946419, 6 pages.
European Patent Office, Examination Report dated Aug. 11, 2010 in European Patent Application No. EP03719056, 4 pages.
European Patent Office, Examination Report dated Aug. 24, 2006 in European Patent Application No. EP99946419, 6 pages.
European Patent Office, Examination Report dated Aug. 25, 2004 in European Patent Application No. EP98204113, 4 pages.
European Patent Office, Examination Report dated Aug. 8, 2005 in European Patent Application No. 98 204 133, 3 pages.
European Patent Office, Examination Report dated Feb. 11, 2009 in European Patent Application No. EP01925833, 4 pages.
European Patent Office, Examination Report dated Feb. 18, 2010 in European Patent Application No. EP0916050, 9 pages.
European Patent Office, Examination Report dated Feb. 27, 2008 in European Patent Application No. EP99946419, 7 pages.
European Patent Office, Examination Report dated Jul. 14, 2009 in European Patent Application No. EP03719056, 6 pages.
European Patent Office, Examination Report dated Mar. 17, 2006 in European Patent Application No. 98 204 133, 3 pages.
European Patent Office, Examination Report dated Mar. 30, 2010 in European Patent Application No. EP05737664, 5 pages.
European Patent Office, Examination Report dated Mar. 9, 2006 in European Patent Application No. EP06100566, 6 pages.
European Patent Office, Examination Report dated May 24, 2007 in European Patent Application No. EP06100566, 3 pages.
European Patent Office, Examination Report dated Oct. 20, 2010 in European Patent Application No. EP06100566, 6 pages.
European Patent Office, Examination Report dated Oct. 26, 2010 in European Patent Application No. EP05737664, 3 pages.
European Patent Office, Examination Report dated Sep. 30, 2011 in European Patent Application No. EP05737664, 5 pages.
European Patent Office, Examination Report dated Sep. 9, 2011 in European Patent Application No. EP0916050, 6 pages.
European Patent Office, Extended European Search Report dated Aug. 3, 2008 in European Patent Application No. EP8158218, 2 pages.
European Patent Office, Extended European Search Report dated Feb. 27, 2009 in European Patent Application No. ep03719056, 6 pages.
European Patent Office, Extended European Search Report dated Jan. 24, 2011 in European Patent Application No. EP10182338, 8 pages.
European Patent Office, Extended European Search Report dated Jun. 22, 2009 in European Patent Application No. EP0916050, 8 pages.
European Patent Office, Extended European Search Report dated Nov. 15, 2010 in European Patent Application No. EP10159373, 12 pages.
European Patent Office, Extended European Search Report dated Sep. 6, 2011 in European Patent Application No. EP03719056, 6 pages.
European Patent Office, Extended European Search Report dated Sep. 6, 2011 in European Patent Application No. EP1117466, 6 pages.
European Patent Office, Office Action dated Aug. 31, 2007 in European Patent Application No. 98 204 1119, 3 pages.
European Patent Office, Office Action dated Sep. 3, 2008 in European Patent Application No. 98 204 1119, 2 pages.
European Patent Office, Supplementary European Search Report dated Feb. 2, 2010 in European Patent Application No. EP03719056, 3 pages.
European Patent Office, Supplementary European Search Report dated May 11, 2000 in European Patent Application No. 98 204 133, 3 pages.
European Patent Office, Supplementary European Search Report dated Nov. 28, 2007 in European Patent Application No. EP01925833, 3 pages.
European Patent Office, Supplementary European Search Report dated Nov. 6, 2009 in European Patent Application No. EP05737664, 7 pages.
Extended European Search Report from Appl. No. EP 09758027.8 dated Jan. 26, 2017.
Herman, G.T. et al., Basic Methods of Tomography and Inverse Problems, Hildger, 1987, 5 pages.
Herman, G.T. et al., Discrete Tomography, Birkhauser, 1999, 3 pages.
Higgins, W.E. et al., "3D CT-Video Fusion for Image-Guided Bronchoscopy," Comput Med Imaging Graph Apr. 2008; 32(3):159-73, 30 pages.
Japan Patent Office, Official Action dated Jul. 3, 2009 in Japanese Patent Application Serial No. JP2005-001768, 6 pages.
Japan Patent Office, Official Action dated Jul. 31, 2009 in Japanese Patent Application Serial No. 2005-005767, 6 pages.
Japan Patent Office, Official Action dated Jun. 19, 2009 in Japanese Patent Application Serial No. JP2005-001769, 2 pages.
Natterer, F., The Mathematics of Computerized Tomography, Wiley, 1989, 4 pages.
Ost et al., "Evaluation and Management of the Solitary Pulmonary Nodule," Am J Respir Crit Care Med vol. 162, pp. 782-787, Sep. 2000, 5 pages.
Palagyi, K. et al., "Quantitative analysis of pulmonary airway tree structures," Computers in Biology and Medicine 36 (2006) 974-996, Sep. 2006, 23 pages.
Ramm, G. et al., The Radon Transform and Local Tomography, CRC Press, 1996, 10 pages.
Shmarak, Itzhak et al., U.S. Appl. No. 10/986,567, filed Nov. 10, 2004 (abandoned, unpublished), 84 pages.
U.S. Appl. No. 09/463,176, filed Jan. 21, 2000 (now U.S. Pat. No. 6,711,429 issued Mar. 23, 2004), 107 pages.
U.S. Appl. No. 09/463,177, filed Jan. 21, 2000 (now U.S. Pat. No. 6,593,884 issued Jul. 15, 2003), 66 pages.

(56) References Cited

OTHER PUBLICATIONS

United States Patent and Trademark Office, Final Office Action dated Apr. 23, 2012 in U.S. Appl. No. 12/170,385, 15 pages.
United States Patent and Trademark Office, Final Office Action dated Aug. 7, 2009 in U.S. Appl. No. 11/427,353, 7 pages.
United States Patent and Trademark Office, Final Office Action dated Dec. 10, 2010 in U.S. Appl. No. 12/503,045, 11 pages.
United States Patent and Trademark Office, Final Office Action dated Dec. 15, 2011 in U.S. Appl. No. 12/369,466, 11 pages.
Extended European Search Report issued in corresponding EP Application No. 18215857.6 dated Sep. 17, 2019, 13 pages.

* cited by examiner

HYBRID REGISTRATION METHOD

RELATED APPLICATIONS

This application is a continuation of U.S. patent application Ser. No. 15/055,698 filed Feb. 29, 2016, which is a continuation of U.S. patent application Ser. No. 13/875,685 filed May 2, 2013, now U.S. Pat. No. 9,271,803, which is a continuation of U.S. Pat. No. 8,452,068 filed Nov. 2, 2011, which is a divisional application of U.S. Pat. No. 8,218,847 filed Jun. 4, 2009, which claims priority to U.S. Provisional Application Ser. No. 61/059,669 filed Jun. 6, 2008, the contents of each of which are incorporated herein by reference.

BACKGROUND

Breakthrough technology has emerged which allows the navigation of a catheter tip through a tortuous channel, such as those found in the pulmonary system, to a predetermined target. This technology compares the real-time movement of a sensor against a three-dimensional digital map of the targeted area of the body (for purposes of explanation, the pulmonary airways of the lungs will be used hereinafter, though one skilled in the art will realize the present invention could be used in any body cavity or system: circulatory, digestive, pulmonary, to name a few).

Such technology is described in U.S. Pat. Nos. 6,188,355; 6,226,543; 6,558,333; 6,574,498; 6,593,884; 6,615,155; 6,702,780; 6,711,429; 6,833,814; 6,947,788; and 6,996,430, all to Gilboa or Gilboa et al.; and U.S. Published Applications Pub. Nos. 2002/0193686; 2003/0074011; 2003/0216639; 2004/0249267 to either Gilboa or Gilboa et al. All of these references are incorporated herein in their entireties.

Using this technology begins with recording a plurality of images of the applicable portion of the patient, for example, the lungs. These images are often recorded using CT technology. CT images are two-dimensional slices of a portion of the patient. After taking several, parallel images, the images may be "assembled" by a computer to form a three-dimensional model, or "CT volume" of the lungs.

The CT volume is used during the procedure as a map to the target. The physician navigates a steerable probe that has a trackable sensor at its distal tip. The sensor provides the system with a real-time image of its location. However, because the image of the sensor location appears as a vector on the screen, the image has no context without superimposing the CT volume over the image provided by the sensor. The act of superimposing the CT volume and the sensor image is known as "registration."

Sensor Probe-Based Registration Methods

There are various registration methods, some of which are described in the aforementioned references, and utilize a probe with a trackable sensor, as described above. For example, point registration involves selecting a plurality of points, typically identifiable anatomical landmarks, inside the lung from the CT volume and then using the sensor (with the help of an endoscope) and "clicking" on each of the corresponding landmarks in the lung. Clicking on the landmarks refers to activating a record feature on the sensor that signifies the registration point should be recorded. The recorded points are then aligned with the points in the CT volume, such that registration is achieved. This method works well for initial registration in the central area but as the sensor is navigated to the distal portions of the lungs, the registration becomes less accurate as the distal airways are smaller. Also, the point registration method matches a "snapshot" location of the landmarks to another "snapshot" (CT volume) of the lungs. Each snapshot is taken at different times and, potentially, at different points in the breathing cycle. Due to the dynamic nature of the lungs, the shape of the lungs during the CT scan is likely not the same as the shape of those same lungs during the procedure. Moreover, because the physician is "clicking" on the landmarks over the course of several breathing cycles, it is up to the physician to approximate the timing of his clicking so that it roughly matches the point in the breathing cycle at which the CT scan was taken. This leaves much room for error. Finally, it is time consuming for the physician to maneuver the sensor tip to the various landmarks.

Another example of a registration method utilizing a trackable sensor involves recording a segment of an airway and shape-match that segment to a corresponding segment in the CT volume. This method of registration suffers similar setbacks to the point registration method, though it can be used in more distal airways because an endoscope is not required. The registration should be conducted more than once to keep the registration updated. It may be inconvenient or otherwise undesirable to require additional registration steps from a physician. Additionally, this method requires that a good image exists in the CT volume for any given airway occupied by the sensor. If for example, the CT scan resulted in an airway shadowed by a blood vessel, for example, the registration will suffer because the shape data on that airway is compromised.

Another registration method tailored for trackable sensors is known as "Adaptive Navigation" and was developed and described in U.S. Published Application 2008/0118135 to Averbuch et al., incorporated by reference herein in its entirety. This registration technique operates on the assumption that the sensor remains in the airways at all times. The position of the sensor is recorded as the sensor is advanced, thus providing a shaped historical path of where the sensor has been. This registration method requires the development of a computer-generated and automatically or manually segmented "Bronchial Tree" (BT). The shape of the historical path is matched to a corresponding shape in the BT.

Segmenting the BT involves converting the CT volume into a series of digitally-identified branches to develop, or "grow," a virtual model of the lungs. Automatic segmentation works well on the well-defined, larger airways and smaller airways that were imaged well in the CT scans. However, as the airways get smaller, the CT scan gets "noisier" and makes continued automatic segmentation inaccurate. Noise results from poor image quality, small airways, or airways that are shadowed by other features such as blood vessels. Noise can cause the automatic segmentation process to generate false branches and/or loops—airways that rejoin, an occurrence not found in the actual lungs.

Another registration method is herein referred to as "feature-based registration." When the CT scans are taken, the CT machine records each image as a plurality of pixels. When the various scans are assembled together to form a CT volume, voxels (volumetric pixels) appear and can be defined as volume elements, representing values on a regular grid in three dimensional space. Each of the voxels is assigned a number based on the tissue density Housefield number. This density value can be associated with gray level or color using well known window-leveling techniques.

The sensing volume of the electromagnetic field of the sensor system is also voxelized by digitizing it into voxels of a specific size compatible with the CT volume. Each voxel visited by the sensor can be assigned a value that correlates to the frequency with which that voxel is visited by the sensor. The densities of the voxels in the CT volume are adjusted according to these values, thereby creating clouds of voxels in the CT volume having varying densities. These voxels clouds or clusters thus match the interior anatomical features of the lungs.

By using a voxel-based approach, registration is actually accomplished by comparing anatomical cavity features to cavity voxels, as opposed to anatomical shapes or locations to structure shapes or locations. An advantage of this approach is that air-filled cavities are of a predictable range of densities.

Image-Based Registration Methods

Some registration methods are used with systems that use a bronchoscope without a trackable sensor. One of these registration methods compares an image taken by a video camera to a virtual model of the airways. The virtual model includes surfaces, reflections and shadows. This method while herein be referred to as "virtual surface matching." A virtual camera is established to generate a viewpoint and a virtual light source is used to provide the reflections, shadows, and surface texture. The virtual camera and light source are matched to the actual video camera and light source so that an "apples to apples" comparison can be performed. Essentially, the virtual model is a library of thousands of computer-generated images of the lungs, from various viewpoints. Hence, the image taken by the video camera is compared against this large library, in the same way a fingerprint is lifted from a crime scene and compared against a large database of fingerprint images. Once the match is found, the camera is determined to be where the "virtual camera" was when the computer image was generated.

One problem with this method is that each time the camera moves, as it is being advanced toward the target, the images recorded by the camera are compared against the large library of computer generated images. This is time consuming and places a strain on the computer resources. It also presents the risk that there may be more than one computer-generated image that closely matches the actual image. For example, if the video camera is up against an airway wall, there may not be much on the image to distinguish it from other similar computer generated images of walls.

Another problem is lack of tracking. Without a sensor, there is no recorded history. Hence, even though the camera is moving and being registered, as soon as the camera encounters an area that matches more than one computer generated image, the registration is lost. The system has no capacity for "tracking" the movement of the camera. In other words, the system does not look at the previous matches to deduce which of the possible images is likely to be the correct one.

Yet another bronchoscope registration method involves terrain or skeletal surface-matching. The virtual model of the lungs is left in a skeletal format, rather than filling the contours in with surfaces and reflections. This saves on initial processing time. As video images are captured of the actual lungs, they are converted into skeletal, digital images. The "real" skeletal images are then matched against the virtual skeletal images. This method requires more processing of the video images than the previously described "virtual surface geometery matching" method but the matching steps are accomplished much more quickly because each of the virtual images is smaller in terms of data. Like the virtual surface matching method, this method present the risk that there may be more than one computer-generated image that closely matches the acquired image, such as when the camera is pointing at a wall.

Each of the aforementioned registration methods has advantages and disadvantages over the others. Generally, the methods using trackable sensors are more accurate than the image-based methods. More particularly, the methods using trackable sensors are more accurate "globally," that is, they are more accurate when it comes to indicating the present position on a scan of the entire lungs. Image-based methods, on the other hand, can be more accurate "locally," that is, they can be more accurate relative to a small area, if conditions are optimal. Thus, it would be advantageous to introduce a hybrid method that utilizes the advantages of all of the aforementioned methods.

SUMMARY

The present invention provides several new or improved registration methods. Additionally, the present invention describes a concept whereby a most accurate registration is determined and utilized at any given time during a procedure, thereby utilizing the advantages of all of the aforementioned registration methods.

More specifically, one aspect of the present invention provides a method of registering real-time sensor location data to previously acquired images of a branched network of body lumens. This method involves placing a probe containing a sensor at a distal end thereof into a branched network of body lumens in a patient; performing an initial registration between a real-time sensor location and a previously acquired image selected a plurality of previously acquired images of said branched network; receiving data from said sensor to determine an approximate location of said sensor; using said approximate location of said sensor to create a subgroup of said plurality of images, said subgroup containing one or more previously acquired images corresponding to said approximate location; and selecting an image from said subgroup that most accurately corresponds to said approximate location to update said initial registration using an image-based registration technique.

Placing a probe containing a sensor at a distal end thereof may comprise placing a probe with a six degree of freedom sensor at a distal end thereof.

Performing an initial registration may comprise viewing a landmark through an endoscope; using data from said sensor to project a beam from a tip of said probe to said landmark; displaying said beam on a monitor; calculating and recording coordinates of said beam location on said landmark; and using said coordinates as a registration point.

Receiving data from said sensor to determine a proximate location of said sensor may comprise receiving six degree of freedom data from said sensor.

Placing a probe containing a sensor at a distal end thereof into a branched network of body lumens may comprise placing a bronchoscope containing a sensor at a distal end thereof into said branched network of body lumens.

Selecting an image from said subgroup that most accurately corresponds to said approximate location to update said initial registration using an image-based registration technique may comprise selecting an image from said subgroup that most closely matches an image being viewed through said bronchoscope.

Performing an initial registration between a real-time sensor location and a previously acquired image selected a plurality of previously acquired images of said branched network may comprise performing an initial registration using a 4D registration technique.

Performing an initial registration using a 4D registration technique may comprise: recording an image of a landmark as it moves through at least one breathing cycle; recording concurrently a position of said sensor; recording concurrently positions of patient sensors, said patient sensor attached at various locations on said patient; saving said recordings as a data set for said landmark; and using said data set to correlate said position of said sensor to a previously acquired image of said branched network of body lumens.

Another aspect of the present invention provides method of navigating a probe through a branched network of lumens of a patient comprising: compiling a database of images of said branched network of lumens prior to a navigating procedure; placing a probe containing a sensor at a distal end thereof into said branched network; receiving probe location data from said sensor; and using at least said probe location data to select an image from said database to display to a user navigating said probe, said image being representative of a location of said probe.

Compiling a database of images of said branched network of lumens prior to a navigating procedure may comprise compiling a plurality of CT scans.

Placing a probe containing a sensor at a distal end thereof into said branched network may comprise placing a probe containing a six degree of freedom sensor at a distal end thereof into said branched network.

Placing a probe containing a sensor at a distal end thereof into said branched network may comprise placing an endoscope containing a sensor at a distal end thereof into said branched network.

Receiving probe location data from said sensor may comprise receiving said probe's location and orientation from said sensor.

Using at least said probe location data to select an image from said database to display to a user navigating said probe, said image being representative of a location of said probe may comprise using said probe location data to create a subgroup of images from said database, said subgroup containing only images that correspond to a vicinity of said probe location.

Placing a probe containing a sensor at a distal end thereof into said branched network may comprise placing an endoscope containing a sensor at a distal end thereof into said branched network.

Using at least said probe location data to select an image from said database to display to a user navigating said probe, said image being representative of a location of said probe further may comprise matching a real-time image from said endoscope to an image from said subgroup.

Another aspect of the present invention provides a method of registering real-time sensor location data to previously acquired images of a branched network of body lumens comprising: placing a probe containing a sensor at a distal end thereof in branched network of body lumens in a patient; placing a plurality of patient sensors on said patient; recording an image of an anatomical landmark in said patient as said landmark moves through at least one breathing cycle; recording concurrently a position of said sensor; recording concurrently positions of patient sensors, said patient sensor attached at various locations on said patient; saving said recordings as a data set for said landmark; and using said data set to correlate said position of said sensor to a previously acquired image of said branched network of body lumens.

Placing a plurality of patient sensors on said patient may comprise affixing said plurality of patient sensors to said patient's chest or affixing a plurality of patient sensors to said branched network.

Using said data set to correlate said position of said sensor to a previously acquired image of said branched network of body lumens may comprise using said data set to correlate said position of said sensor to a previously acquired CT image of said branched network of body lumens.

DETAILED DESCRIPTION

The sensor based and image-based registration methods described above are improved upon by combining the advantages of each. Put another way, the image-based registration techniques are improved upon through the use of a trackable sensor. By monitoring sensor data, an approximate position of the probe tip is easily determined. Hence, a database of virtual images may be appropriately parsed such that the matching algorithm has a significantly reduced number of iterations through which it must cycle to find a match. The position of the sensor is thus used as filtering tool to determine which images are locally relevant.

Additionally, the tracking of a tool tip or bronchoscope location will not be lost in cases of partial or complete obscurity of the video image or in cases when the bronchoscope is passing a bifurcation while the camera is pointed away from the bifurcation toward a wall. Due to the tracking capability provided by the trackable sensor, the number of matching images will typically be reduced to only one after the outliers are removed. Hence, not only is the matching procedure much quicker, it is also more accurate and less likely to provide incorrect matches.

The image-based registration methods are further improved because the need for camera calibration is eliminated. Presently, image-based registration methods require extensive camera calibration efforts, prior to each procedure, in order to obtain images that can be matched to the virtual images. Factors such as camera angle and camera distortion must be corrected prior to the matching process. Because the use of the trackable sensor as an additional modality greatly reduces the amount of data involved, calibration is much less crucial. In other words, despite forgoing the calibration step, a match is still likely to be found and accurate because the number of images the camera image is being compared to is greatly reduced.

The point registration method described above is also improved by the present invention. Recall that presently the point registration method is comprised of two general steps: 1) finding a predetermined anatomical landmark using a bronchoscope and 2) "click" on the landmark by advancing the probe with the trackable sensor until it touches the landmark, then press a button that records the three-dimensional coordinates of the landmark. The present invention obviates the need for the second step by utilizing the six degree of freedom data provided by the sensor once the landmark is being viewed through the bronchoscope. This data is used to project a virtual "beam" from the tip of the probe to the target. The virtual beam appears on the monitor and the physician is then able to record the coordinates of the landmark without actually having to maneuver the probe into physical contact with the landmark.

The present invention also provides a novel registration method, herein referred to as "4D registration." Rather than clicking on a landmark at an approximated point in the breathing cycle, video registration involves recording an image of a landmark as it moves through at least one, preferably two or more, breathing cycles. The recording of the landmark includes a recording of the position of the trackable sensor as well as the positions of the patient sensors. This way, rather than acquiring a single data coordinate for each landmark, an entire data set is recorded for each landmark over a period of time and including all or most of the possible lung positions. This way lung movement may be taken into account during the registration process. Furthermore, the matching error will be minimized if an entire data set is used for each point, rather than a single, three-dimensional coordinate.

For example, assume three registration areas are being monitored. The positions of all three are recorded over three separate intervals. The patient sensor positions are also being recorded during each of these intervals as well as the position of the trackable sensor and attached to each image frame. After the three registration points have been recorded over one or more breathing cycles, they are aligned using the patient sensor positions as an indication of the breathing cycle. Hence, for most of the positions of the patient sensors (extremes excepted), there will be a corresponding position of each of the sensors. Hence, the three intervals during which the recordings were taken are "superimposed" so to speak, as though they were all recorded simultaneously. Later, during the procedure, the patient sensor positions are used as an indication of breathing cycle and it can be determined at which phase of the breathing cycle the registration is most accurate. Moreover, this information can be utilized during navigation by giving the higher weight to sensor data acquired in a specific phase of breathing.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A system for registering sensor location data to images of at least one body part, comprising:
   an endoscope including:
      a sensor configured to generate data corresponding to a location of the sensor relative to at least one body part in a patient, and
      an image sensor configured to generate image data; and
   a computing device having a memory configured to store a plurality of previously acquired images of the at least one body part, and including thereon a software application that, when executed by the computing device,
      displays a three-dimensional (3D) model derived from the plurality of previously acquired images,
      detects a location of the sensor,
      receives image data from the image sensor, and
      registers the location of the sensor to a subgroup of images selected from the plurality of previously acquired images, wherein registration is achieved by parsing the plurality of previously acquired images based on the location data to generate the subgroup of the plurality of previously acquired images, and comparing images in the subgroup to images received from the image sensor to identify an image that substantially matches an image generated by the image sensor.

2. The system of claim 1, wherein the software application, when executed by the computing device, displays the previously acquired image after the comparison confirms a substantial match.

3. The system of claim 1, wherein the software application, when executed by the computing device, updates an initial registration of the location of the sensor based on comparisons to the images in the subgroup with images from the image sensor.

4. The system of claim 3, wherein the updating of the initial registration commences on detecting a change in location of the sensor.

5. The system of claim 1, wherein detecting the location of the sensor requires recording a segment of an airway and shape-matching the segment to a segment in the 3D model.

6. The system of claim 1, wherein the sensor is an electromagnetic sensor and generating location data includes sensing electromagnetic fields.

7. The system of claim 1, wherein the previously acquired images are virtual images generated from computer tomography (CT) images stored in memory, and a matching virtual image defines a subgroup of the virtual images corresponding to the detected location of the sensor.

8. The system of claim 7, wherein the software application, when executed by the computing device, selects a virtual image from the subgroup of the virtual images that most accurately corresponds to the detected location of the sensor to update an initial registration using an image-based registration technique when the endoscope and the sensor are moved.

9. The system of claim 7, wherein the virtual images and the subgroup are stored in a database.

10. The system of claim 1, wherein the subgroup is a single image.

11. The system of claim 10, wherein the single image is displayed.

12. The system of claim 1, wherein generating data corresponding to a location of the sensor relative to at least one body part in a patient includes recording a segment of an airway and shape-matching the segment to a segment in the 3D model.

* * * * *